(12) United States Patent
Mizutani et al.

(10) Patent No.: US 8,715,474 B2
(45) Date of Patent: May 6, 2014

(54) GAS SENSOR ELEMENT AND METHOD OF DETECTING CONCENTRATION OF TARGET DETECTION GAS

(75) Inventors: Keigo Mizutani, Okazaki (JP); Takehiro Watarai, Kuwana (JP); Norikazu Kajiyama, Chiryu (JP)

(73) Assignee: Denso Corporation, Kariya (JP)

( * ) Notice: Subject to any disclaimer, the term of this patent is extended or adjusted under 35 U.S.C. 154(b) by 33 days.

(21) Appl. No.: 13/411,743

(22) Filed: Mar. 5, 2012

(65) Prior Publication Data

US 2012/0228154 A1     Sep. 13, 2012

(30) Foreign Application Priority Data

Mar. 7, 2011  (JP) ................................. 2011-048644

(51) Int. Cl.
*G01N 27/407*     (2006.01)
(52) U.S. Cl.
USPC ........... 204/424; 204/425; 204/426; 204/427; 204/428; 204/429; 73/23.31; 73/23.32
(58) Field of Classification Search
USPC ........................ 204/424–429; 73/23.31–23.32
See application file for complete search history.

(56) References Cited

U.S. PATENT DOCUMENTS

| | | | | |
|---|---|---|---|---|
| 4,264,425 A | * | 4/1981 | Kimura et al. | 204/412 |
| 4,579,643 A | * | 4/1986 | Mase et al. | 204/427 |
| 6,936,148 B2 | * | 8/2005 | Mabuchi et al. | 204/425 |
| 2003/0205078 A1 | * | 11/2003 | Hasei et al. | 73/23.31 |
| 2003/0221975 A1 | | 12/2003 | Mizutani et al. | |

FOREIGN PATENT DOCUMENTS

| JP | 2003-185624 | 7/2003 |
|---|---|---|
| JP | 2004-53579 | 2/2004 |
| JP | 2004-163254 | 6/2004 |

OTHER PUBLICATIONS

Office Action (2 pgs.) dated Jan. 7, 2014 issued in corresponding Japanese Application No. 2011-048644 with an at least partial English-language translation thereof (2 pgs.).

* cited by examiner

*Primary Examiner* — Bach Dinh
(74) *Attorney, Agent, or Firm* — Nixon & Vanderhye PC

(57) ABSTRACT

A gas sensor element has a first cell, a second cell, and a solid electrolyte layer having proton conductivity commonly used by the first cell and the second cell. The first cell has a first cathode and a first anode exposed to the target detection gas containing hydrogen atoms. The second cell has a second anode, a second cathode, and a shield layer with which the second anode is covered. A voltage is supplied to the first and second cells. A gas concentration of the target detection gas is calculated on the basis of a difference between a current of the first cell and a current of the second cell because the current in the first cell is a sum of proton conductivity current and an electron conductivity current. The current in the second cell is an electron conductive current only.

8 Claims, 5 Drawing Sheets

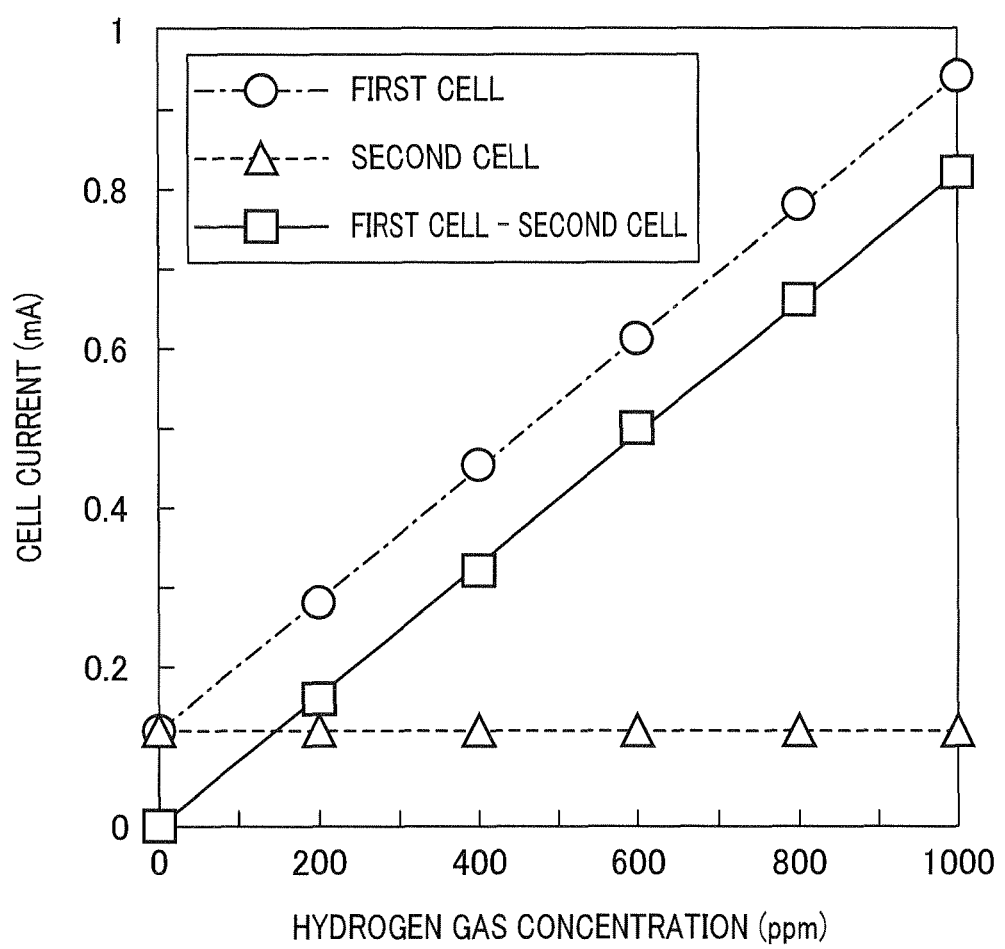

GAS SENSOR ELEMENT AND METHOD OF DETECTING CONCENTRATION OF TARGET DETECTION GAS

CROSS-REFERENCE TO RELATED APPLICATION

This application is related to and claims priority from Japanese Patent Application No. 2011-48644 filed on Mar. 7, 2011, the contents of which are hereby incorporated by reference.

BACKGROUND OF THE INVENTION

1. Field of the invention

The present invention relates to gas sensor elements equipped with a solid electrolyte having proton conductivity and methods of detecting a concentration of a component contained in target detection gas by using a gas sensor element.

2. Description of the Related Art

Air pollution is the introduction of chemicals, particulate matter, or biological materials emitted from internal combustion engines for motor vehicles, etc., that causes harm or discomfort to humans or other living organisms, or causes damage to the natural environment or built environment, into the atmosphere. Pollution control standards acts and regulations on chemicals, particulate matter, or biological materials contained in exhaust gas emitted from internal combustion engines for motor vehicles become stricter year by year.

For example, there have been proposed various types of gas sensor elements and techniques which directly detect a concentration of a component contained in exhaust gas such as nitrogen oxide (NOx) gas, hydrogen gas, hydrocarbon, etc. and transmit detected data to an engine combustion control monitor, a catalyst monitor, etc. It is therefore necessary from the above views to provide a gas sensor element capable of detecting a concentration of hydrogen gas and hydrocarbon, etc. contained in exhaust gas as a target detection gas to be detected.

There is a conventional technique, disclosed in Japanese patent laid open publication No. JP 2003-185624, which provides a moisture tester capable of detecting a quantity of moisture contained in a target detection gas to be detected. However, the moisture tester does not detect a concentration of hydrogen gas or hydrocarbon gas. Such a conventional moisture tester has a solid layer of a proton conductive type installed between two positive electrodes and a negative electrode. The two positive electrodes are made of an electron conductivity material. A block layer is formed between one positive electrode and the solid layer. The block layer substantially blocks the proton conductivity between the positive electrode and the solid layer.

The conventional moisture tester disclosed in Japanese patent laid open publication No. JP 2003-185624 detects a first current in an electric circuit containing one positive electrode in which the block layer is formed and detects a second current flowing through an electric circuit containing the other positive electrode in which no block layer is formed. The moisture tester detects a current generated by the proton conductivity on the basis of a difference between the first current value and the second current value. The moisture tester can detect a content of water in the target detection gas to be detected with high accuracy.

A known conventional gas sensor element using the solid electrolyte having proton conductive type has the following drawback. A current generated by the proton conductivity flows in a solid electrolyte layer in a conventional gas sensor element in addition to a current generated by the electron conductivity. It is necessary for the conventional gas sensor element to detect a concentration of a target detection gas containing hydrogen atoms on the basis of a detected current value which corresponds to the sum of a current generated by the proton conductivity and a current generated by the electron conductivity. It is therefore difficult to detect the concentration of a target detection gas containing hydrogen atoms on the basis of the current sum of the proton conductivity and the electron conductivity with high accuracy.

The moisture tester disclosed in Japanese patent laid open publication No. JP 2003-185624 introduces proton through a side part of the positive electrode and the block layer. This decreases the detection accuracy when it detects hydrogen gas or hydrocarbon gas.

SUMMARY

It is therefore desired to provide a novel gas sensor element and a method of detecting a concentration of target detection gas containing hydrogen atoms with high accuracy by using the novel gas sensor element.

An exemplary embodiment provides a gas sensor element having a first cell, a second cell, and a solid electrolyte layer having proton conductivity. The solid electrolyte layer is commonly used by the first cell and the second cell. The first cell has a first anode (as a first positive electrode) and a first cathode (as a first negative electrode). The first anode is formed on one surface of the solid electrolyte layer and is exposed to a target detection gas containing hydrogen atoms. The first cathode is formed on the other surface of the solid electrolyte layer. The second cell has a second anode (as a second positive electrode), a second cathode (as a second negative electrode), and a shield layer impermeable to gas. The second anode is formed on one surface of the solid electrolyte layer. The second cathode is formed on the other surface of the solid electrolyte layer. The second anode of the second cell is covered with the shield layer.

Another exemplary embodiment provides a method of detecting a concentration of a target detection gas by using the gas sensor element. The method has the following three steps. A first step supplies a predetermined voltage to the first cell and detects a current sum of a proton conductive current flowing in the solid electrolyte layer and an electron conductive current flowing in the solid electrolyte layer. The second step supplies a predetermined voltage to the second cell and detects an electron conductive current flowing in the solid electrolyte layer. The third step calculates a difference between the current sum as the current flowing in the first cell obtained in the first step and the current flowing in the second cell obtained by the second step, and detects a concentration of the target detection gas containing hydrogen atoms on the basis of the calculated difference.

BRIEF DESCRIPTION OF THE DRAWINGS

A preferred, non-limiting embodiment of the present invention will be described by way of example with reference to the accompanying drawings, in which:

FIG. 3 is a view showing a relationship between a cell current and a concentration of hydrogen gas as a target detection gas when the gas sensor element according to the first exemplary embodiment detects a concentration of hydrogen gas by using a gas concentration detection method;

DETAILED DESCRIPTION OF THE PREFERRED EMBODIMENTS

Figure 1A:
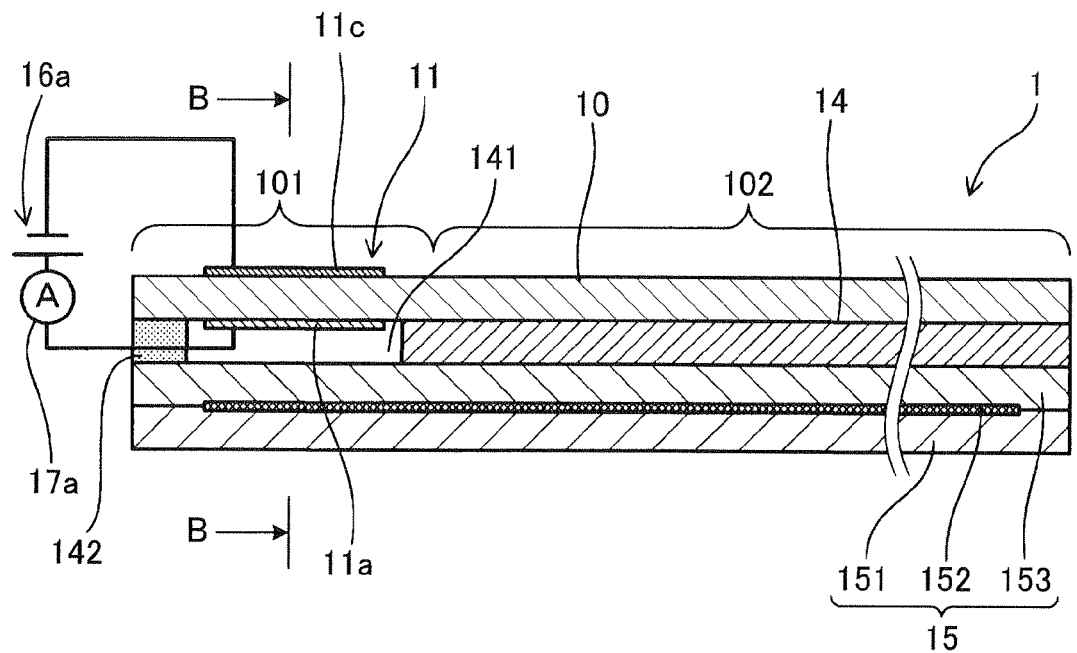
FIG. 1A is a view showing a schematic cross section along a longitudinal direction of a gas sensor element according to a first exemplary embodiment of the present invention.

Hereinafter, various embodiments of the present invention will be described with reference to the accompanying drawings. In the following description of the various embodiments, like reference characters or numerals designate like or equivalent component parts throughout the several diagrams.

First Exemplary Embodiment

A description will be given of the gas sensor element 1 and a method of detecting a concentration of a target detection gas to be detected according to the first exemplary embodiment of the present invention with reference to FIG. 1A, FIG. 1B, FIG. 2 and FIG. 3.

Figure 1B:
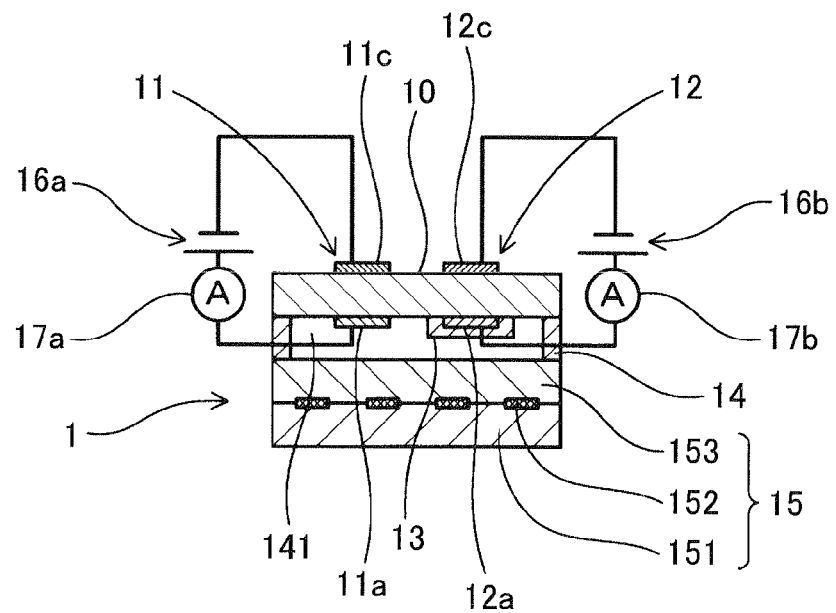
FIG. 1B is a view showing a schematic cross section of the gas sensor element along the B-B line shown in FIG. 1A.

FIG. 1A is a view showing a schematic cross section along a longitudinal direction of the gas sensor element 1 according to the first exemplary embodiment. FIG. 1B is a view showing a schematic cross section of the gas sensor element 1 along the B-B line shown in FIG. 1A.

As shown in FIG. 1A and FIG. 1B, the gas sensor element 1 according to the first exemplary embodiment has a solid electrolyte layer 10, a first cell 11 and a second cell 12. The first cell 11 and the second cell 12 commonly use the solid electrolyte layer 10 having proton conductivity. In the first exemplary embodiment, the solid electrolyte layer 10 has a sheet shape made of perovskite oxide material expressed by a compositional formula of $SrZr_{0.9}Yb_{0.1}O_{2.95}$. The solid electrolyte layer 10 has a thickness of 200 μm.

As shown in FIG. 1A and FIG. 1B, the first cell 11 is composed of the solid electrolyte layer 10, a first anode 11a (as a first positive electrode 11a) and a first cathode 11c (as a first negative electrode 11c).

The first anode 11a is formed on one side of the solid electrolyte layer 10 so that the first anode 11a faces a target detection gas containing hydrogen atoms such as hydrogen gas in a penetration hole 141 (or a target detection gas chamber 141) which will be explained later. The first cathode 11c is formed on the other surface of the solid electrolyte layer 10.

On the other hand, as shown in FIG. 1B, the second cell 12 is composed of the solid electrolyte layer 10, a second anode 12a (as a second positive electrode 12a) and a second cathode 12c (as second negative electrode 12c), and a shield layer 13. The second anode 12a is formed on one side of the solid electrolyte layer 10. The second cathode 12c is formed on the other surface of the solid electrolyte layer 10. The second anode 12a is covered with the shield layer 13 so that the shield layer 13 faces hydrogen gas containing hydrogen gas as a target detection gas to be detected in the penetration hole 141 as the target detection gas chamber. That is, the shield layer 13 covers the entire surface of the second anode 12a in order to protect the second anode 12a from the hydrogen gas introduced into the target detection gas chamber.

In the structure of the gas sensor element 1 according to the first exemplary embodiment, the first anode 11a and the second anode 12a have the same layer shape, the same size and the same area. The first cathode 11c and the second cathode 12c also have the same layer shape, the same size and the same area.

In particular, each of the first anode 11a, the first cathode 11c, the second anode 12a and the second cathode 12c is made of porous cermet of Pt and $SrZr_{0.9}Yb_{0.1}O_{2.95}$.

Further, each of the first anode 11a, the first cathode 11c, the second anode 12a and the second cathode 12c has a thickness of 10 μm.

The shield layer 13 is made of alumina and has a layer structure having a thickness of 20 μm.

A description will now be given of the detailed explanation of the gas sensor element 1 according to the first exemplary embodiment.

As shown in FIG. 1, the solid electrolyte layer 10, a spacer 14, a heater part 15 which are laminated in order to produce a lamination. The solid electrolyte layer 10 is composed of the first cell 11 and the second cell 12. The first cell 11 and the second cell 12 are formed at the front part of the gas sensor element 1.

The spacer 14 is installed between the solid electrolyte layer 10 and the heater part 15 in order to form the target detection gas chamber 141. In the structure of the gas sensor element 1 according to the first exemplary embodiment, the spacer 14 has a sheet shape and is made of alumina. It is also possible to provide the spacer 14 made of other electrical insulation material instead of alumina. The spacer layer 14 has a thickness of 200 μm. The spacer 14 has the penetration hole 141 whose cross section is a rectangular shape. The penetration hole 141 is used as the target detection gas chamber.

A diffusion layer 142 is formed at the front part of the spacer 14 which forms the penetration hole 141, that is, the target detection gas chamber 141 communicates with the external space, in which a target detection gas is present, through the diffusion layer 142. The target detection gas is introduced into the inside of the target detection gas chamber 141 through the diffusion layer 142. In the structure of the gas sensor element 1 according to the first exemplary embodiment, the first anode 11a of the first cell 11 is formed in the target detection gas chamber 141. In the target detection gas chamber 141, the second anode 12a of the second cell 12 is arranged so that the second anode 12a is adjacent to the first anode 11a of the first cell 11.

In the structure of the gas sensor element 1 according to the first exemplary embodiment, the diffusion layer 142 is a porous layer made of alumina. It is also possible to provide the diffusion layer 142 made of other material other than alumina. The diffusion layer 142 has a thickness of 200 μm which is the same thickness of the spacer 14. The diffusion layer 142 has a porosity of 40%, and a pore diameter within a range of 1 to 5 μm.

The heater part 15 is composed of a base layer 151, a heater electrode 152 and an insulation layer 153. The heater electrode 152 has a pattern structure and is formed on one surface of the base layer 151. The insulation layer 153 is formed on the base layer 151, on which the heater electrode 152 is also formed. When receiving electric power, the heater part 15 generates heat energy to increase a temperature of each of the first cell 11 and the second cell 12 to an activation temperature.

The base layer 151 and the insulation layer 153 are made of alumina. Each of the base layer 151 and the insulation layer 153 has a thickness of 200 μm. The heater electrode 152 is made of cermet composed of Pt and alumina. The heater electrode 152 has a thickness of 30 μm.

The gas sensor element 1 according to the first exemplary embodiment has the structure to transmit various signals between the first cell 11, the second cell 12, the heater part 15 and external devices (not shown).

Figure 2:
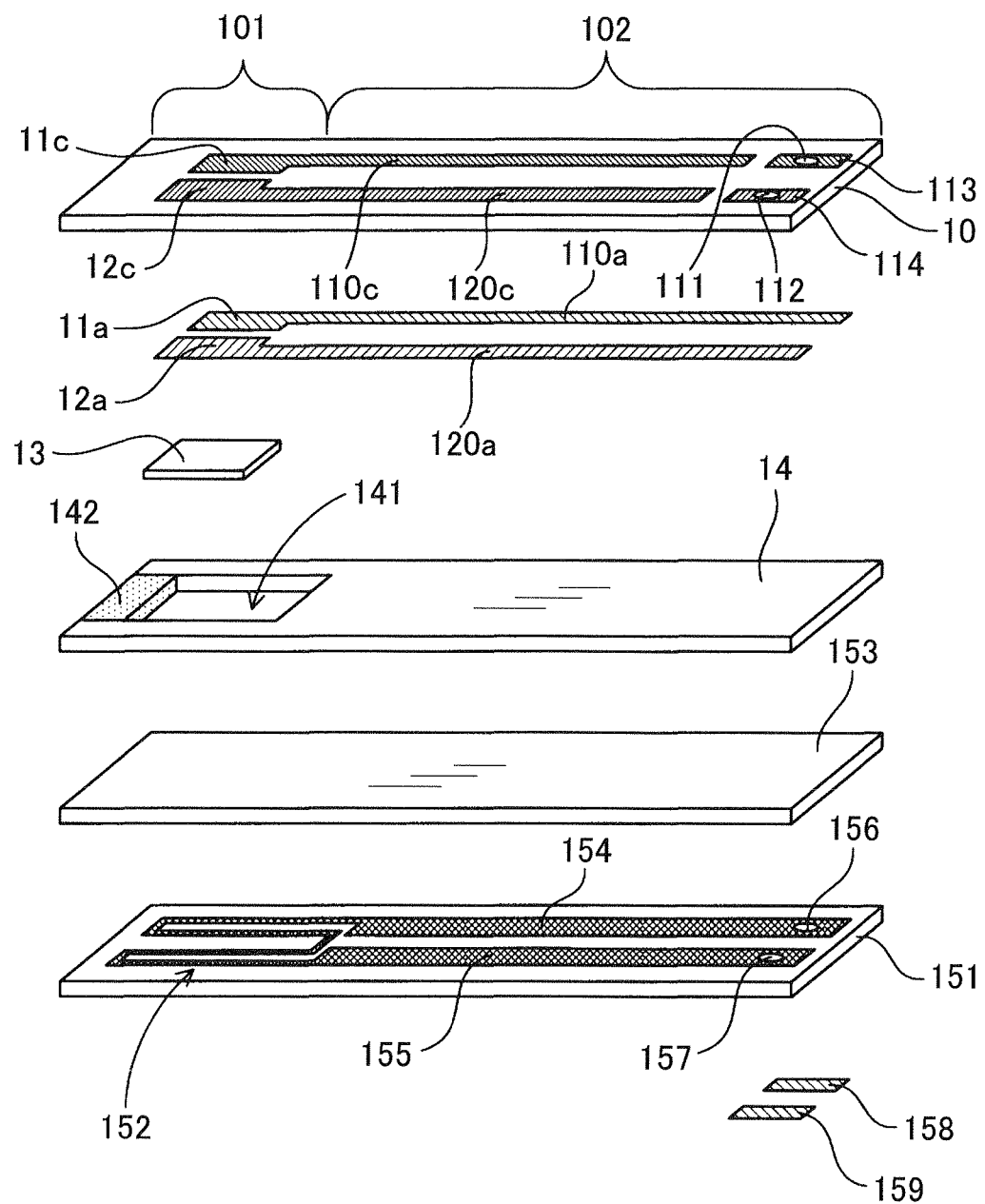
FIG. 2 is a schematic development view showing a structure of the gas sensor element according to the first exemplary embodiment shown in FIG. 1A and FIG. 1B.

FIG. 2 is a schematic development view showing a structure of the gas sensor element 1 according to the first exemplary embodiment shown in FIG. 1A and FIG. 1B.

Specifically, as shown in FIG. 2, the solid electrolyte layer 10 has a cell formation part 101 at the front part thereof and a circuit formation part 102 at a distal end part thereof. The first cell 11 and the second cell 12 are formed in the cell formation part 101. A connection circuit is formed in the circuit formation part 102.

A lead 110a and a lead 120a are formed on one surface of the circuit formation part 102. One end of the lead 110a and one end of the lead 120a are connected to the first anode 11a and the second anode 12a, respectively.

The other end of the lead 110a and the other end of the lead 120a are connected to pad electrodes 113 and 114, respectively, through through-holes 111 and 112 formed at the distal end part of the circuit formation part 102. The pad electrodes 113 and 114 are formed on the other surface of the circuit formation part 102. The leads 110a and 120a are electrically connected to an outside circuit (not shown) through the pad electrodes 113 and 114.

Further, a lead 110c and a lead 120c are formed on the other surface of the circuit formation part 102. One end of the lead 110c and one end of the lead 120c are connected to the first cathode 11c and the second cathode 12c, respectively. The other end of the lead 110c and the end of the lead 120c are extended to the distal end part side of the circuit formation part 102. Through the lead parts 110c and 120c, the first cathode electrode 11c and the second cathode electrode 12c are electrically connected to the outside circuit (not shown).

Still further, a lead 154 and a lead 155 are formed on the surface of the base layer 151, on which the heater electrode 151 is also formed. One end of the lead 154 is connected to one end of the heater electrode 152, and one end of the lead 155 is connected to the other end of the heater electrode 152.

The other end of the lead 154 is connected to a pad electrode 158 through a through-hole 156 formed in the base layer 151. The pad electrode 158 is formed on the other surface of the base layer 151, which is opposite to the surface of the base layer 151 on which the heater electrode 152 is formed. The lead 154 is connected to an external circuit (not shown) through the through-hole 156 and the pad electrode 158.

Similarly, the other end of the lead 156 is connected to a pad electrode 159 through a through-hole 157 formed in the base layer 151. The pad electrode 159 is formed on the other surface of the base layer 151, which is opposite to the surface of the base layer 151 on which the heater electrode 152 is formed. The lead 155 is connected to an external circuit (not shown) through the through-hole 157 and the pad electrode 159.

The lead 110a, the lead 110c, the lead 120a, the lead 120c, the lead 154, the lead 155, the heater electrode 152 and each of the pad electrodes 113, 114, 158 and 158 are formed by screen printing.

A description will now be given of the method of producing the gas sensor element 1 according to the first exemplary embodiment.

Each of sheets, having the solid electrolyte layer 10, the spacer 14, the diffusion layer 142, and the heater part 15 (which is composed of the base layer 151 and the insulation layer 153) was produced by a doctor blade method.

Next, the first anode 11a, the first cathode 11c, the second anode 12a, the second cathode 12c, the shield layer 13, leads 110a, 110c, 120a, 120c, 154 and 155, the heater electrode 152, the pad electrodes 113, 114, 158 and 159, etc. are formed in a predetermined pattern on the corresponding sheets previously produced by a screen printing method. The sheets were stacked to make a lamination. The obtained lamination was fired at a temperature of 1500° C. over ordinary predetermined hours in order to produce the gas sensor element 1.

A description will now be given of the action and effects of the gas sensor element 1 according to the first exemplary embodiment produced by the above method.

A target detection gas containing hydrogen atoms to be detected is introduced into the inside of the target detection gas chamber 141 through the diffusion layer 142. A quantity of the target detection gas is determined by a diffusion resistance value of the diffusion layer 142.

A predetermined DC voltage of a DC power source 16a is supplied between the first anode 11a and the first cathode 11c of the first cell 11 so that the first anode 11a has a positive electrode.

When such a predetermined voltage is supplied to the first cell 11, hydrogen atoms are separated from the target detection gas on the surface of the first anode 11a and protons are generated. The generated protons pass through the solid electrolyte layer 10 and are exhausted to the first cathode 11c side. When the generated proton atoms pass through the solid electrolyte layer 10, a cell current flows in the inside of the first cell 11. The magnitude of the generated cell current depends on a concentration of the target detection gas. It is therefore possible to detect a concentration of the target detection gas on the basis of the magnitude of the cell current flowing through the solid electrolyte layer 10.

The first exemplary embodiment uses hydrogen gas as the target detection gas. By the way, the voltage is changed by a kind of the target detection gas containing hydrogen atoms, in which the voltage is supplied between the first anode 11a and the first cathode 11c in the first cell 11 in order to separate protons from hydrogen gas as the target detection gas on the surface of the first anode 11a. It is thereby possible to adjust the voltage supplied to the first anode 11a and the first cathode 11c in the first cell 11 in order to selectively detect a concentration of a different target detection gas However, because the solid electrolyte layer 10 has electron conductivity in addition to having proton conductivity, the cell current passing through the first cell 11 detected by an ammeter 17a is a sum of a current generated by the electron conductivity (which will also be referred to as the "electron current") and a current generated by the proton conductivity (which will also be referred to as the "proton conductive current") in the first cell 11.

Because the electron conductive current, which is generated by the electron conductivity in the first cell 11, does not depend on the concentration of a target detection gas, there is a possibility of generating incorrect detection on the basis of a detected-error by the electron conductive current.

By the way, the gas sensor element 1 according to the first exemplary embodiment is composed of the second cell 12 in addition to the first cell 11. The second anode 12a of the second cell 12 is covered with the shield layer 13. The shield layer 13 has gas impermeability. In the first exemplary embodiment, a predetermined DC voltage of the DC power source 16b is supplied between the second anode 12a and the second cathode 12c of the second cell 12 so that the second anode 12a has a positive electrode. Even if such a predetermined voltage is supplied to the second cell 12, an electron conductive current generated by the electron conductivity flows in the second cell 12, but no proton conductive current flows in the second cell 12 because the second anode 12a is covered with the shield layer 13 impermeable to gas. That is, because the entire outer surface of the second anode 12a is covered with the shield layer 13, no excess protons are introduced into the inside of the second anode 12a through the side part thereof, like the case disclosed in the patent document 1, as previously described. Accordingly, as shown in FIG. 1B, an ammeter 17b can detect the electron conductive current as the cell current generated in the second cell 12 by the electron conductivity only.

It is therefore possible to calculate a difference between the cell current flowing in the first cell 11 and the cell current flowing in the second cell 12, and to detect only the proton conductive current generated by the proton conductivity on the basis of the calculated current difference. The gas sensor element 1 according to the first exemplary embodiment can detect a concentration of a target detection gas (such as hydrogen gas) with high accuracy.

Next, a description will now be given of the method of detecting a concentration of the target detection gas. The method detects a concentration of a target detection gas by using the gas sensor element 1 according to the first exemplary embodiment.

The method basically has the following three steps, namely, a first step, a second step, and a third step.

The first step supplies a predetermine voltage to the first cell 11 of the gas sensor element 1 and detects a current sum between a proton conductive current generated by proton conductivity of the solid electrolyte layer 10 and an electron conductive current generated by electron conductivity.

The second step supplies a predetermine voltage to the second cell 12 of the gas sensor element 1 and detects an electron conductive current generated by electron conductivity of the solid electrolyte layer 10.

The third step calculates a difference between the current flowing in the first cell 11 and the current flowing in the second cell 12. The third step detects, namely, calculates a concentration of a target detection gas containing hydrogen atoms on the basis of the current difference calculated above.

Specifically, in the first step, the predetermined voltage is supplied between the first anode 11a and the first cathode 11c of the first cell 11 so that the first anode 11a of the first cell 11 has a positive electrode. This allows the ammeter 17a to detect a sum of the electron conductive current and the proton conductive current which flow in the first cell 11.

Next, in the second step, the predetermined voltage is supplied between the second anode 12a and the second cathode 12c of the second cell 12 so that the second anode 12a of the second cell 12 has a positive electrode. This allows the ammeter 17b to detect an electron conductive current which flow in the second cell 12.

Next, in the third step, a concentration of the target detection gas containing hydrogen atoms is calculated on the basis of the difference between the current detected by the ammeter 17a and the current detected by the ammeter 17b.

FIG. 3 is a view showing a relationship between a cell current and a concentration of hydrogen gas when the gas sensor element 1 according to the first exemplary embodiment detects a concentration of hydrogen gas by the method of detecting a gas concentration of a target detection gas.

In this case, a voltage of 0.4V was supplied to each of the first cell 11 and the second cell 12. A hydrogen gas having a concentration within a range of 0 to 1000 ppm was used as the target detection gas. Nitrogen gas was used as balance gas.

As shown in FIG. 3, the cell current flowing in the first cell 11 is a sum of a proton conductive current and an electron conductive current. In particular, the proton conductive current depends on a concentration of the target detection gas. The reference character "○" shows the characteristics of the proton conductive current. Because the electron conductive current fluctuates, namely, changes depending on cell temperature, the electron conductive current generates a detection error, namely, causes a wrong detection.

On the other hand, because the second anode 12a is covered with the shield layer 13 in the second cell 12, the second anode 12a is not exposed directly to the hydrogen gas as the target detection gas introduced into the inside of the target detection gas chamber 141. In other words, the second anode 12a is not in contact with the hydrogen gas. Because the second cell 12 does not trap any protons from the hydrogen gas, no proton current flows in the second cell 12. The electron conductive current only flows as the cell current in the second cell 12. The electron conductive current flowing in the second cell 12 has characteristics designated by the reference character "Δ" shown in FIG. 3. The reference character "□" indicates a difference between the cell current in the first cell 11 and the cell current in the second cell 12. The difference between the cell current in the first cell 11 and the cell current in the second cell 12 is free from any influence of the electron conductive current. As described above, it is possible for the method according to the first exemplary embodiment to detect a concentration of hydrogen gas as the target detection gas with high accuracy.

Second Exemplary Embodiment

A description will be given of the gas sensor element 1-1 having a first cell 11-1 and a second cell 12-1 according to the second exemplary embodiment of the present invention with reference to FIG. 4A and FIG. 4B.

Figure 4A:
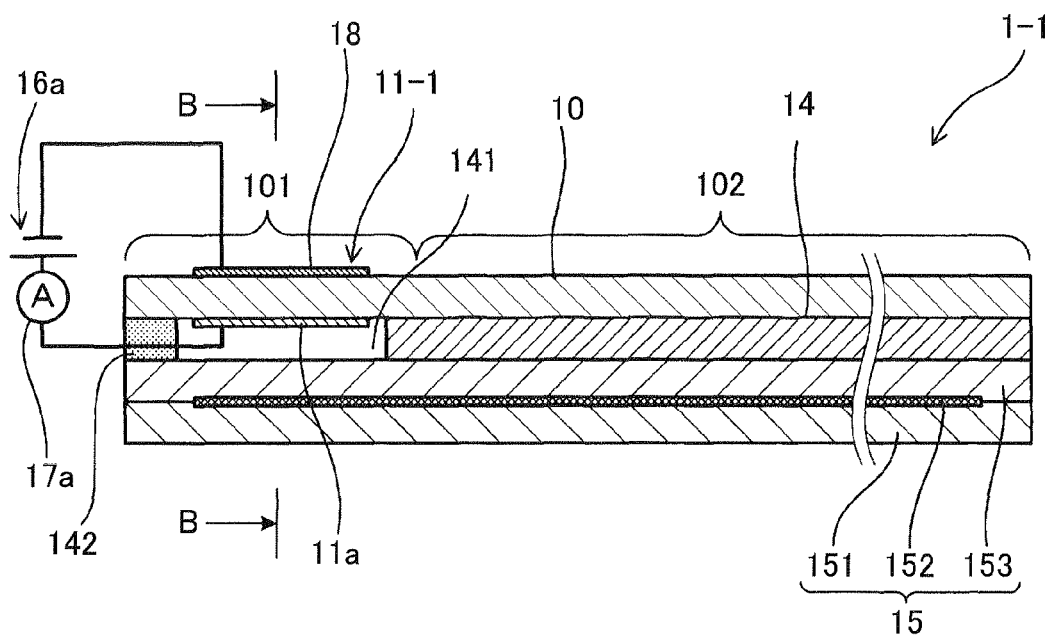
FIG. 4A is a view showing a schematic cross section along a longitudinal direction of a gas sensor element according to a second exemplary embodiment of the present invention.

FIG. 4A is a view showing a schematic cross section along a longitudinal direction of the gas sensor element 1-1 according to the second exemplary embodiment. FIG. 4B is a view showing a schematic cross section along the B-B line shown in FIG. 4A.

In the second exemplary embodiment, the first cell 11-1 and the second cell 12-1 has a common cathode 18 (as a common negative electrode 18), which is different in structure from the first cell 11 and the second cell 12 having the first cathode 11c and the second cathode 12c according to the first exemplary embodiment shown in FIG. 1A and FIG. 1B.

Figure 4B:
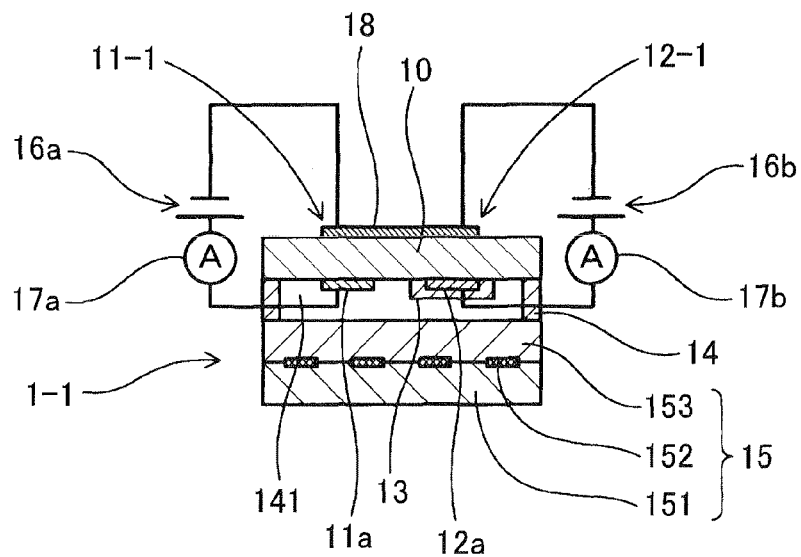
FIG. 4B is a view showing a schematic cross section along the B-B line shown in FIG. 4A.

As shown in FIG. 4A and FIG. 4B, the first cell 11-1 and the second cell 12-1 have the common cathode 18. In other word, the first cathode of the first cell 11-1 is joined to the first cathode of the second cell 12-1. Other components of the gas sensor element 1-1 according to the second exemplary embodiment are the same of those of the gas sensor element 1 according to the first exemplary embodiment.

Because the first cell 11-1 and the second cell 12-1 have the common cathode 18, it is possible to decrease the number of signal terminals, and to have a simple structure. This structure further improves a manufacturing workability of producing the gas sensor element. Still further, the method according to the first exemplary embodiment, previously described can use the gas sensor element 1-1 according to the second exemplary embodiment in order to detect a concentration of the target detection gas containing hydrogen atoms with high accuracy.

Third Exemplary Embodiment

A description will be given of the gas sensor element 1-2 having a first cell 11-2 and a second cell 12-2 according to the third exemplary embodiment of the present invention with reference to FIG. 5A and FIG. 5B.

Figure 5A:
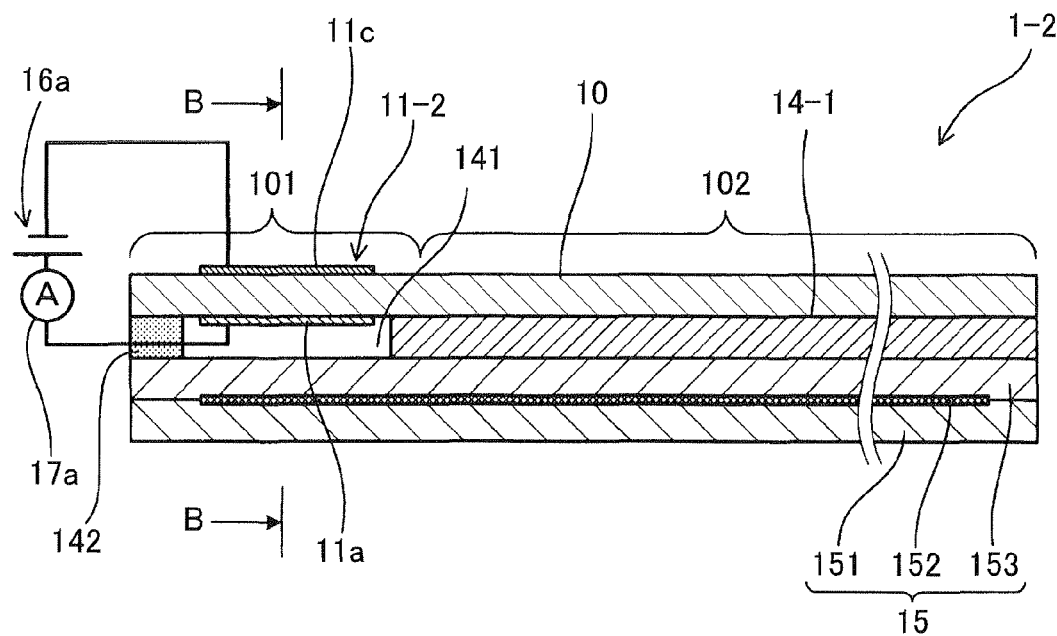
FIG. 5A is a view showing a schematic cross section along a longitudinal direction of a gas sensor element according to a third exemplary embodiment of the present invention.

FIG. 5A is a view showing a schematic cross section along a longitudinal direction of the gas sensor element 1-2 according to the third exemplary embodiment of the present invention. FIG. 5B is a view showing a schematic cross section along the B-B line shown in FIG. 5A.

The gas sensor element 1-2 according to the third exemplary embodiment has a shield layer 13-1, a spacer 14-1 and a target detection gas chamber 141-1 which are different in structure from the gas sensor element 1 according to the first exemplary embodiment shown in FIG. 1A and FIG. 1B.

Figure 5B:
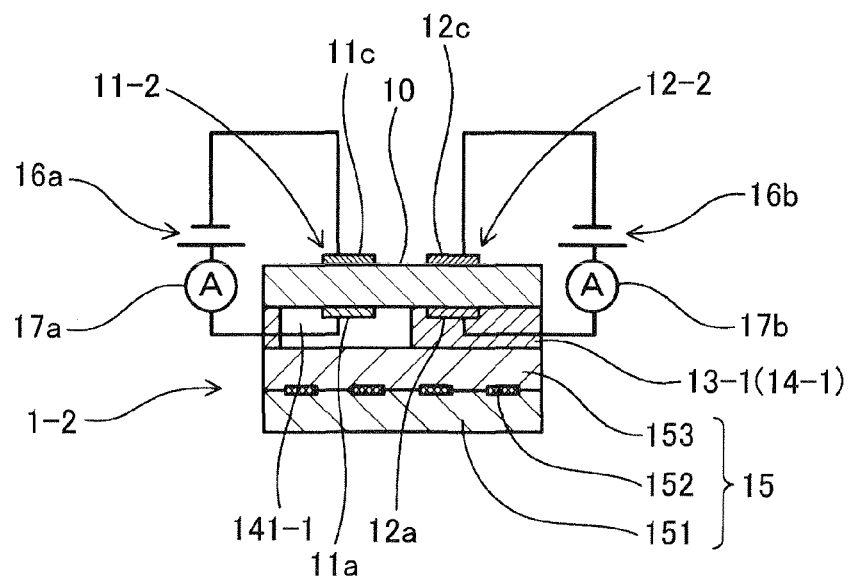
FIG. 5B is a view showing a schematic cross section along the B-B line shown in FIG. 5A.

As shown in FIG. 5A and FIG. 5B, a part of the spacer is used as a part of the shield layer in the structure of the gas sensor element 1-2 according to the third exemplary embodiment. That is, the first anode 11*a* of the first cell 11-2 is only arranged in the target detection gas chamber 141-1 so that the first anode 11*a* is exposed to the target detection gas in the target detection gas chamber 141-1. Further, the second anode 12*a* of the second cell 12-2 is covered with the spacer 14-1 as the shield layer 13-1. That is, the spacer 14-1 also acts as the shield layer 13-1. Other components of the gas sensor element 1-2 according to the third exemplary embodiment are the same of those of the gas sensor element 1 according to the first exemplary embodiment.

In the structure of the gas sensor element 1-2 according to the third exemplary embodiment, the second anode 12*a* of the second cell 12-2 is covered with the spacer 14-1 as the shield layer 13-1. This makes it possible to completely isolate the second anode 12*a* from the target detection gas introduced into the target detection gas chamber 141-1. That is, it is possible to securely separate the second anode 12*a* of the second cell 12-2 from the target detection gas by the spacer 14-1 having a large thickness, when compared with the thickness of the shield layer 13 in the gas sensor element 1. Further, because the shield layer 13-1 and the spacer 14-1 are made of same material and formed together simultaneously, it is possible to enhance the efficiency of the manufacturing workability and to decrease the manufacturing cost. Other features and effects of the gas sensor element 1-2 according to the third exemplary embodiment are the same of those of the gas sensor element 1 according to the first exemplary embodiment. Still further, the method described in the description of the first exemplary embodiment can detect a concentration of the target detection gas containing hydrogen atoms with high accuracy by using the gas sensor element 1-2 according to the third exemplary embodiment.

(Features and Effects of the Gas Sensor Element and the Method According to the Present Invention)

When the predetermined voltage is supplied to the first cell in the gas sensor element 1 according to the present invention, the target detection gas containing hydrogen atoms is decomposed, and a cell current flows in the first cell. Since the solid electrolyte layer 10 has electron conductivity in addition to proton conductivity, the total cell current flowing in the first cell 11 is a sum of the proton conductive current and the electron conductive current. On the other hand, because the second anode 12*a* of the second cell 12 is completely covered with the shield layer 13, the electron conductive current flows in the second cell 12, but no proton conductive current flows in the second cell 12. Accordingly, it is possible to detect a current value of the proton conductive current on the basis of a difference between the cell current in the first cell 11 and the cell current in the second cell 12. That is, this makes it possible to avoid the influence of the electron conductive current and to obtain the current value of the proton conductive current with high accuracy. It is therefore possible for the gas sensor element 1 according to the present invention to detect a concentration of the target detection gas containing hydrogen atoms with high accuracy on the basis of such a current difference.

Further, the method according to the present invention uses the gas sensor element 1 having the structure previously described. The method supplies the predetermined voltage to the first cell 11 in order to detect a current as a sum of a proton conductive current and an electron conductive current in the solid electrolyte layer 10 of the first cell 11. Further, the method supplies the predetermined voltage to the second cell 12 to detect an electron conductive current only in the solid electrolyte layer of the second cell 12. Finally, the method calculates a difference of the sum of the current obtained in the first cell 11 and the current value obtained in the second cell 12, and calculates a concentration of the target detection gas on the basis of the calculated difference. This makes it possible to avoid the influence of the electron conductive current in the solid electrolyte layer 10 and to detect a concentration of the target detection gas with high accuracy on the basis of the current value of the proton conductive current only.

It is therefore possible for the method according to the present invention to detect a concentration of the target detection gas containing hydrogen atoms with high accuracy.

As previously described, the gas sensor element 1 according to the present invention has the first cell 11 and the second cell 12 which have the same solid electrolyte layer 10 having proton conductivity. That is, the solid electrolyte layer 10 is commonly used in the first cell 11 and the second cell 12. That is, the first cell 11 uses a part of the solid electrolyte layer 10 and the second cell 12 uses the remaining part of the solid electrolyte layer 10. The solid electrolyte layer 10 has the electron conductivity in addition to the proton conductivity (as a proton-electron mixture conductive material).

For example, the solid electrolyte layer 10 composed of base material such as perovskite oxide material of a compositional formula such as $SrZrO_3$, $CaZrO_3$, $BaCeO_3$ and $SrCeO_3$.

A concrete compositional formula of the perovskite oxide material can be expressed by the following formula, $SrZr_{1-x}M_xO_{3-\alpha}$, $CaZr_{1-x}M_xO_{3-\alpha}$, $BaCe_{1-x}M_xO_{3-\alpha}$, and $Sr_{1-x}CeMxO_{3-\alpha}$. It is acceptable for the solid electrolyte to contain one or more kinds of the above perovskite oxide materials, where M is one or more elements selected from Y, Yb, In, Sc, Dy and Gd. It is preferable that X is within a range of 0.05 to 0.2, more preferable within a range of 0.10 to 0.20, and $\alpha = X/2$.

It is preferable for the gas sensor element to have the solid electrolyte layer having a thickness within a range of 10 to 1000 μm, more preferable within a range of 50 to 500 μm, or most preferable within a range of 100 to 300 μm.

Further, it is preferable for the gas sensor element to have the solid electrolyte layer of a plane shape such as a sheet shape.

It is possible to produce the solid electrolyte layer by using a doctor blade method. The doctor blade method molds a slurry containing solid electrolyte powder of perovskite oxide material into a sheet, and fires the produced sheet. It is also possible to use an extrusion molding method to extrude such slurry into a sheet. The solid electrolyte powder can be produced to mix department raw materials such as perovskite oxide material having a compositional formula such as $SrZrO_3$, $CaZrO_3$, $BaCeO_3$, $SrCeO_3$, fires the obtained mixture, and crushes the mixture into fragments so as to make a mixture powder after the firing step.

Still further, it is also possible to produce such a mixture power by a liquid phase process of a coprecipitation method using nitrate solution in liquid phase process.

The gas sensor element according to the present invention has a novel structure having the solid electrolyte layer, the first cell and the second cell. The first cell has the first anode and the first cathode. The first anode is formed on one surface of the solid electrolyte layer so as to be exposed directly to the target detection gas containing hydrogen atoms such as hydrogen gas introduced into the inside of the target detection gas chamber 141. Further, the first cathode is formed on the other surface of the solid electrolyte layer.

On the other hand, the second cell has the solid electrolyte layer, the second anode and the second cathode. In particular, the solid electrolyte layer is commonly used by the first cell and the second cell.

The second anode is formed on one surface of the solid electrolyte layer. The second cathode is formed on the other surface of the solid electrolyte layer. In particular, the second anode has a unique and novel structure, that is, the second anode is completely covered with the shield layer impermeable to gas.

That is, in more detail, the first anode of the first cell and the second anode of the second cell are formed on the other surface (namely, on the same surface) of the solid electrolyte layer. The first cathode of the first cell and the second cathode of the second cell are formed on one surface (namely, on the same surface) of the solid electrolyte layer. The surface of the solid electrolyte layer on which the first anode and the second anode are formed is opposite to the other surface of the solid electrolyte layer on which the first cathode and the second cathode are formed. In other words, the first cell has a structure in which the solid electrolyte layer is formed between the first anode and the first cathode which face together through the solid electrolyte layer, where the first cathode and the first anode make a pair. On the other hand, the second cell has a structure in which the solid electrolyte layer is formed between the second anode and the second cathode which face together through the solid electrolyte layer, where the second cathode and the second anode make a pair. As described above, the solid electrolyte layer is commonly used by the first cell and the second cell. It is preferable to form the first cell and the second cell which are adjacent to each other so that the first cell and the second cell have the same detection condition to detect the concentration of the target detection gas.

It is preferable that the first anode, the second anode, the first cathode and the second cathode have the same shape, and the same surface area. This structure makes it possible to have the same electron conductive current in the first cell and the second cell, and to increase the detection accuracy of detecting a concentration of the target detection gas. However, even if the above electrodes have a different shape and an area, it is possible to detect a concentration of the target gas with high accuracy by using a coefficient corresponding to the difference in shape and area of those electrodes In view of electrical resistance and gas permeability, it is preferable for each of the electrodes of the first cell and the second cell to have a thickness within a range of 1 to 20 µm, more preferable to have a thickness within a range of 5 to 15 µm. It is also possible to form each of the electrodes in the first cell and the second cell by using noble metal such as Pt and Pd, porous cermet as a mixture of noble metal and ceramics such as $SrZrO_3$, $CaZrO_3$, $BaCeO_3$, $SrCeO_3$, or by using porous cermet composed of the above noble metal and the material to be used for producing the solid electrolyte layer. The solid electrolyte layer is commonly used in the first cell and the second cell. Each of the electrodes in the first cell and the second cell is produced by a screen printing method.

It is possible that the first cathode and the second cathode are formed independently to each other, or formed to join them together. When the first cathode and the second cathode are formed to join together, the first cathode and the second cathode are formed makes a common cathode (as a common negative electrode) in the first cell and the second cell. This makes it possible to decrease the number of components in the gas sensor element and to provide a simple structure of the gas sensor element. Further, this structure can decrease the number of terminals of the gas sensor element and to decrease the manufacturing cost and to increase manufacturing workability.

In use of the gas sensor element, the first anode of the first cell is directly exposed to target detection gas containing hydrogen atoms. It is possible to apply the gas sensor element to various types of gas containing hydrogen atoms such as hydrogen gas, hydrocarbon gas, vapor or steam. It is preferable to use the gas sensor element in order to detect a concentration of hydrogen gas.

On the other hand, the second anode of the second cell is completely covered with the shield layer impermeable to gas. That is, the second anode is not exposed directly to the target detection gas containing hydrogen atoms introduced in the inside of the target detection gas chamber. That is, no target gas containing hydrogen atoms is supplied to the surface of the second anode of the second cell.

It is sufficient for the target detection gas to be exposed directly to (namely, to be in contact only with) the first anode of the first cell in the gas sensor element. Therefore it is possible for the gas sensor element to have various structures. For example, it is possible to arrange the first anode and the second anode in the same space in which the target detection gas is present. It is also possible to have a structure in which the first anode of the first cell is only arranged in the gas chamber in which the target detection gas is present.

It is preferable for the gas sensor element according to the present invention to further have the diffusion layer and the target detection gas chamber. The target detection gas chamber communicates with an external space through the diffusion layer. The target detection gas in the external space is introduced into the inside of the target detection gas chamber through the diffusion layer. At least the first anode of the first cell is installed in the inside of the target detection gas chamber so that the first anode of the first cell is exposed to the target detection gas, In the structure of the gas sensor element, the target detection gas in the outer space is introduced at a predetermined diffusion speed into the target detection gas chamber through the diffusion layer. This makes it possible to detect a current value such as proton conductive current and electron conductive current and to avoid occurrence of an incorrect detection. This increases the detection accuracy of the gas sensor element. Further, it is possible to form the target detection gas chamber by the solid electrolyte layer, the heater part and the spacer. The spacer is sandwiched between the solid electrolyte layer and the heater part. When receiving electric power, the heater part generates heat energy to increase the temperature of the first cell and the second cell until an active temperature is reached. The spacer has one or more penetration holes through which lead wires are connected to outside devices.

For example, there is as the external space an exhaust gas system of an internal combustion engine used in motor vehicles and an external device using hydrogen $H_2$ gas, etc.

The diffusion layer made of diffusion material has a predetermined diffusion resistance which allows the target detection gas containing hydrogen atoms to be introduced into the inside of the target detection gas chamber.

It is preferable for the gas sensor element to use the diffusion layer of a porous structure in order to easily obtain a predetermined diffusion resistance. It is possible to determine a shape, a porosity and a diameter or size of pores of the diffusion layer in order to obtain the target detection gas at a predetermined travel speed to be introduced into the inside of the target detection gas chamber through the diffusion layer. For example, there are porous alumina, and perovskite oxide materials such as $SrZrO_3$, $CaZrO_3$, $BaCeO_3$, $SrCeO_3$.

It is preferable that the second anode (as the second positive electrode) electrode of the second cell covered with the shield layer is arranged in the target detection gas chamber.

In this structure of the gas sensor element, because the first anode (as the first positive electrode) of the first cell and the second anode of the second cell are arranged in the same space, it is possible to detect a current flowing in the first cell and a current flowing in the second cell under the same detection environment or condition. This makes it possible to decrease occurrence of an incorrect detection and to increase the detection accuracy when the method uses the gas sensor element and detects a concentration of the target detection gas.

For example, it is possible for the gas sensor element to have another structure in which the spacer is used to shield the second anode of the second cell. That is, the spacer acts as the shield layer. That is, the first anode of the first cell is arranged only in the inside of the target detection gas chamber, the second anode is formed in inside of the spacer. This structure allows the second anode to be covered completely with the spacer as the shield layer and to prevent the second anode of the second cell from being in contact with the target detection gas. That is, this improved structure makes it possible to completely shield and protect the second anode from the target detection gas by using the spacer having a large thickness because the spacer has an adequate thickness to form the target detection gas chamber. Still further, this structure of the gas sensor element makes it possible to increase the manufacturing efficiency and to decrease manufacturing cost because of not being necessary to form the shield layer in addition to the spacer.

The shield layer in the gas sensor element has gas impermeability in which the target detection gas cannot pass through the shield layer. It is preferable to form the shield layer by compact material. It is preferable for the shield layer to have a relative density of not less than 90%, more preferable of not less than 95% in view of guarantee of the gas impermeability. Such a relative density can be detected by using a porosimeter or an image obtained from a SEM (a scanning electron microscope), etc.

It is possible to select one of electrical insulation materials to form the shield layer in view of the feature capable of preventing occurrence of protonation reaction in the shield layer. In order to form the shield layer, it is preferable to select solid electrolyte materials, for example, glass and ceramics such as alumina and mullite.

It is preferable to use a material composed of alumina as a base material when the shield layer is formed between the solid electrolyte and the heater part.

This makes it possible for the shield layer to easily have an electric insulation capability and stable characteristics at a high temperature. The material composed of alumina as a base material is difficult to react with the target detection gas containing hydrogen atoms, and difficult to generate proton on the shield layer. Those features can provide easy detection of an electron conductive current generated in the solid electrolyte in the second cell. This makes it possible to decrease occurrence of an incorrect detection and to increase the detection accuracy.

It is preferable to use the shield layer having a thickness within a range of 5 to 50 μm.

This structure provides a superior condition for the first cell and the second cell to have the same temperature, namely, the condition of decreasing the difference in temperature between the first cell and the second cell. Further, this structure also has the good gas impermeability. This makes it possible to decrease occurrence of an incorrect detection and to increase the detection accuracy.

It is more preferable for the shield layer to have the bottom limit of the thickness of 10 μm, most preferable of the thickness of 15 μm in view of obtaining the gas impermeability. On the other hand, it is more preferable for the shield layer to have the upper limit of the thickness of 40 μm, most preferable of the thickness of 30 μm in view of obtaining the same temperature between the first cell and the second cell.

The present invention provides the method of detecting a concentration of the target detection gas by using the gas sensor element having the novel structure and features previously described. The detection method has the three steps. The first step supplies a predetermined voltage to the first cell, detects a current as a sum of a proton conductive current flowing in the solid electrolyte layer and an electron conductive current flowing in the solid electrolyte layer. The second step supplies a predetermined voltage to the second cell and detects an electron conductive current flowing in the solid electrolyte layer. The third step calculates a difference between the current obtained from the first cell and the current obtained from the second cell, and calculates a concentration of the target detection gas containing hydrogen atoms on the basis of the calculated difference current value.

In the first step, the predetermined voltage to be supplied to the first cell is used as a decomposition voltage for separating hydrogen atoms from the target detection gas containing hydrogen atoms.

In the second step, the predetermined voltage to be supplied to the second cell is the same voltage to be supplied to the first cell. It is possible to select an optional voltage to be supplied to the first cell and the second cell according to a kind of the target detection gas. The voltage to be supplied to the first cell in the first step and the second cell in the second step is adjusted so that each of the first anode and the second anode has a positive electrode.

It is possible to execute the first step, the second step, and the third step in order, and also possible to execute the second step, the first step and the third step in order. Further, it is possible to execute the first step and the second step simultaneously and then to execute the third step.

When the first step and the second step are executed simultaneously, it is possible to detect the current value flowing in the first cell and the current flowing in the second cell in the same detection condition (such as the same temperature). This method decreases occurrence of incorrect detection and to increase the detection accuracy.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A gas sensor element comprising: a solid electrolyte layer having proton conductivity; a first cell; and a second cell, wherein:

the solid electrolyte layer having proton conductivity is commonly used by the first cell and the second cell, the first cell comprises a first anode and a first cathode, the first anode is formed on one surface of the solid electrolyte layer and is exposed to a target detection gas containing hydrogen atoms, the first cathode is formed on the other surface of the solid electrolyte layer, and the second cell comprises a second anode, a second cathode, and a shield layer impermeable to gas, the second anode is formed on one surface of the solid electrolyte layer, the second cathode is formed on the other surface of the solid electrolyte layer, and the second anode of the second cell is covered with the shield layer, the gas sensor element further comprises a diffusion layer and a target detection gas chamber, the target detection gas chamber communicates with an external space through the diffusion layer, the target detection gas in the external space is introduced into the inside of the target detection gas chamber through the diffusion layer, at least the first anode of the first cell is arranged in the inside of the target detection gas chamber so that the first anode of the first cell is exposed to the target detection gas, the gas sensor element further comprises a spacer and a heater layer, the spacer is formed between the solid electrolyte and the heater layer so that the spacer, the diffusion layer, the solid electrolyte and the heater layer form the target detection gas chamber, and wherein the second anode is covered with a part of the spacer which is used as the shield layer.

2. The gas sensor element according to claim 1, wherein the spacer is made of material containing alumina as a main component.

3. The gas sensor element according to claim 1, wherein the spacer has a thickness of 200 μm.

4. The gas sensor element according to claim 1, wherein the first anode in the first cell and the second anode in the second cell have the same shape and the same surface area, and the first cathode in the first cell and the second cathode in the second cell have the same shape and the same surface area.

5. The gas sensor element according to claim 1, wherein each of the first anode, the first cathode, the second anode, and the second cathode has a thickness within a range of 1 to 20 μm.

6. The gas sensor element according to claim 5, wherein each of the first anode, the first cathode, the second anode, and the second cathode has a thickness within a range of 5 to 15 μm.

7. The gas sensor element according to claim 1, wherein the first cathode in the first cell and the second cathode in the second cell are commonly formed together in one electrode.

8. A method of detecting a concentration of a target detection gas by using the gas sensor element according to claim 1, comprising steps of:

supplying a predetermined voltage to the first cell and detecting a current which is a sum of a proton conductive current flowing in the solid electrolyte layer and an electron conductive current flowing in the solid electrolyte layer;

supplying a predetermined voltage to the second cell and detecting an electron conductive current flowing in the solid electrolyte layer; and calculating a difference between the current sum obtained by the first cell and the current obtained by the second cell, and detecting a concentration of the target detection gas containing hydrogen atoms on the basis of the calculated current difference.

* * * * *